US012766231B2

(12) United States Patent
Klöffel et al.

(10) Patent No.: US 12,766,231 B2
(45) Date of Patent: Oct. 20, 2026

(54) DIALYSIS MACHINE

(71) Applicant: Fresenius Medical Care Deutschland GmbH, Bad Homburg (DE)

(72) Inventors: Peter Klöffel, Nüdlingen (DE); Tilman Stäblein, Würzburg (DE); Andreas Syfonios, Bergreinfeld (DE); Dirk Hümmer, Hirschfeld (DE); Tobias Irrgang, Aubstadt (DE); Benedict Glaser, Schweinfurt (DE)

(73) Assignee: FRESENIUS MEDICAL CARE DEUTSCHLAND GMBH, Bad Homburg (DE)

(*) Notice: Subject to any disclaimer, the term of this patent is extended or adjusted under 35 U.S.C. 154(b) by 371 days.

(21) Appl. No.: 18/499,690

(22) Filed: Nov. 1, 2023

(65) Prior Publication Data

US 2024/0139390 A1 May 2, 2024

Related U.S. Application Data

(62) Division of application No. 17/044,882, filed as application No. PCT/EP2019/058317 on Apr. 2, 2019, now Pat. No. 11,839,710.

(30) Foreign Application Priority Data

Apr. 4, 2018 (DE) ..................... 10 2018 107 895.1

(51) Int. Cl.
*A61M 1/16* (2006.01)
*A61M 1/36* (2006.01)

(52) U.S. Cl.
CPC ........ *A61M 1/1635* (2014.02); *A61M 1/1658* (2013.01); *A61M 1/3627* (2013.01); *A61M 2206/16* (2013.01)

(58) Field of Classification Search
CPC .............. A61M 1/1635; A61M 1/1658; A61M 1/3627; A61M 2206/16; B01D 19/0057; B01D 19/0063
See application file for complete search history.

(56) References Cited

U.S. PATENT DOCUMENTS 4,345,919 A * 8/1982 Wilkinson ......... B01D 19/0031 96/209
4,371,382 A 2/1983 Ross
(Continued)

FOREIGN PATENT DOCUMENTS

DE 1766588 8/1971
DE 4329385 3/1995
(Continued)

*Primary Examiner* — Dirk R Bass
(74) *Attorney, Agent, or Firm* — Kilyk & Bowersox, P.L.L.C.

(57) ABSTRACT

The present invention relates to a dialysis machine comprising a balancing system that has at least one balancing chamber for a volumetrically exact supply and removal of dialysis solution to and from a dialyzer fluidically connected to the balancing system in operation; a water inlet system connected to the balancing system for the supply of fresh dialysis liquid, with the water inlet system having an apparatus for degassing water that is connected to an air separator of the dialysis machine, with a first subsection of the air separator serving as a mixing chamber and being connectable to at least one concentrate source via at least one concentrate line and being in fluid communication with the balancing system via at least one dialysate line, wherein the filling volume of a balancing chamber corresponds to or exceeds the sum of the volume of the mixing chamber and the inner volume of the dialysate line.

13 Claims, 4 Drawing Sheets

(56) References Cited

U.S. PATENT DOCUMENTS

| | | | | |
|---|---|---|---|---|
| 2012/0316799 | A1 | 12/2012 | Gagel | |
| 2017/0182233 | A1 | 6/2017 | Kloeffel et al. | |
| 2018/0272054 | A1 * | 9/2018 | Syfonios | A61M 1/1658 |

FOREIGN PATENT DOCUMENTS

| | | | | |
|---|---|---|---|---|
| DE | 102015012604 | A1 * | 3/2017 | A61M 1/1662 |
| EP | 0367252 | | 5/1990 | |
| GB | 1191586 | | 5/1970 | |
| WO | 201705 | | 4/2017 | |

* cited by examiner

DIALYSIS MACHINE

BACKGROUND OF THE INVENTION

1. Field of the Invention

The present invention relates to a dialysis machine comprising a balancing system that has at least one balancing chamber for a volumetrically exact supply and removal of dialysis solution to and from a dialyzer fluidically connected to the balancing system in operation; a water inlet system connected to the balancing system for the supply of fresh dialysis liquid, with the water inlet system having an apparatus for degassing water that is connected to an air separator of the dialysis machine, with a first subsection of the air separator serving as a mixing chamber and being in fluid communication with or fluidically connectable to at least one concentrate source via at least one concentrate line and being in fluid communication with or fluidically connectable to the balancing system via at least one dialysate line.

The water inlet system can optionally have a recirculation circuit for the degassing of water.

An air separator can be located in the water inlet system, with a first subsection of the air separator serving as a mixing chamber and being in fluid communication with or fluidically connected to at least one concentrate source via at least one concentrate line and being in fluid communication with or fluidically connected to the balancing system via at least one dialysate line.

2. Description of Related Art

Such a dialysis machine is known from WO 2017/054923 A1. The dialysis machine known from this document is shown schematically in FIG. 4. The machine in accordance with FIG. 4 has a container 20 that is filled with RO water via the feed line 22. Reference numeral 10 denotes a recirculation and degassing circuit in which a solution or a liquid, in particular RO water, that serves the preparation of the finished dialysis solution circulates by means of the pump P1. In addition to further components, a pressure relief valve V2 and the primary air separator 50, that will also simply be called an "air separator" in the following, are arranged in the recirculation circuit 10. The RO water is degassed and heated in the recirculation circuit 10.

As can further be seen from FIG. 4, a line 23 extends between the container 20 and the recirculation circuit 10 and the fluid inside the container, in particular RO water, is supplied to the recirculation circuit 10 via said line.

A venting line 52 that is closable by a valve V1 and that is opened as required to remove air from the air separator 50 extends from the primary air separator 50 to the water inlet container 20. It should be ensured by the separation of air that fluid or RO water contained in the recirculation circuit is as free of air as possible. The air is released by the degassing of the RO water in that a vacuum that results in the degassing of the RO water is generated by the degassing pump P1 in conjunction with the degassing restrictor 11. A further source for air comprises one of the concentrate containers K1, K2 being empty and thus not concentrate, but air, being conveyed through the concentrate lines 54, 56.

The lines 30 and 32 denote lines for consumed dialysate, i.e. lines that are connected to the dialyzer and through which consumed dialysate from the dialyzer flows. The consumed dialysate moves via the line 32 to the heat exchanger 40 and from there via the line 30 to an outflow 60.

Reference symbol B denotes the balancing system by means of which it is ensured that the dialysate conveyed to the dialyzer is supplied in the same volume as dialysate moving from the dialyzer is drained. Reference symbol D denotes the dialyzer that has a plurality of hollow fiber membranes that are flowed around or through by dialysis solution on the one side and by blood on the other side. As can be seen from the Figure, the dialyzer D is connected to the balancing system B at the inlet side and at the outlet side. Reference symbol P4 denotes the dialysate pump that conveys the dialysate solution. It is arranged downstream of the dialyzer D in the embodiment shown here. The consumed dialysate is thereby filled into the balancing chamber by means of the dialysate pump P4. Fresh dialysate is pumped into the balancing chamber via the liquid pressure generated by the pump P1. The adjustable pressure relief valve V2 can be usable for setting the so-called charging pressure that is generated for filling by the pump P1.

A balancing chamber can consist of a chamber having a predefined volume, whose two halves are separated by a flexible membrane. If a first half of the balancing chamber is filled with liquid at the beginning of a balancing chamber cycle, the volume of this half comprises the total balancing chamber volume while there is very largely no liquid or no liquid at all in the second half. If the second half of the balancing chamber now conveys liquid, the membrane is displaced and the liquid is displaced from the first half. The direction of the flow can be determined by a corresponding valve switching that opens or closes the inflows and outflows to the balancing chamber halves.

Instead of the flexible membrane, a balancing chamber can also have a rigid, displaceable separation plate that is displaced in a cylinder. The two chambers separated by the separation plate then form the balancing chamber halves here. Such balancing chambers are also known as duplex pumps.

Reference symbols K1 and K2 in simplified terms denote concentrate containers, for example, for a base concentrate and an acid concentrate. These containers are connected via lines 54, 56 to the lower section or to the bottom of the air separator 50 in operation of the dialysis machine. The conveying of the concentrates from the concentrate containers K1 and K2 takes place by means of the pumps P2 and P3 through the lines 54 and 56. The connection of the lines 54 and 56 to the corresponding concentrate sources or concentrate containers can be established via concentration suction rods that are arranged at the lines 54 and 56. The pumps P2 and P3 are preferably membrane pumps.

The recirculation into the recirculation circuit 10 effected by the pump P1 is shown by the closed arrow at the center of the recirculation circuit.

In operation of the arrangement shown, RO water is supplied via the line 23 and concentrates are supplied to the lower part of the primary air separator 50 via the lines 54 and 56. The components water and at least one concentrate, preferably two or three concentrates, are transferred for mixing into the lower part of the primary air separator 50. These components flow out of the lower region of the primary air separator 50 via the line 58 into the balancing chamber system B. A correspondingly large volume of RO water can flow on into the recirculation circuit 10 via the line 23.

The separate water inlet circuit, that is also called a recirculation circuit 10 above or has such a recirculation circuit in an embodiment, supplies the balancing chamber B of the machine with temperature-controlled water. If—as stated—solution is removed from the recirculation circuit 10, i.e. is led to the balancing chamber system B, the removed amount from the water inlet chamber 20 is topped up and is preheated by means of the consumed dialysis liquid via the heat exchanger 40.

As can further be seen from FIG. 4, the air separation from the primary air separator 50 takes place in its upper region that, differing from the lower region, is connected to the recirculation circuit or forms its component. The supply of concentrates by means of the lines 54, 56 and the removal of the finished dialysis solution by means of the line 58 takes place from a section of the primary air separation at the bottom with respect to it.

These two sections of the primary air separator 50 are connected to one another by means of a separation plate having openings for the air separation.

It is pointed out that one or more features of the above-described dialysis machine shown in FIG. 4 can also be the subject of the present invention.

The concentrates are typically conveyed from the concentrate containers in individual strokes or part strokes of membrane pumps into the mixing chamber, i.e. into the first subsection of the air separator. The mixing ratio is determined by the number of strokes or the magnitude of the strokes of the pump(s). The concentrates supplied in this manner to the first subsection of the air separator, however, do not mix immediately, but there are concentration gradients. If this inhomogeneous liquid is transferred into a balancing chamber half of the balancing system, there is a need that the volume of liquid actually transferred into the balancing chamber actually comprises the concentrate provided for the upcoming stroke of the balancing chamber at least to a large extent, preferably completely.

SUMMARY OF THE INVENTION

It is thus the underlying object of the invention to further develop a dialysis machine of the initially named kind such that the aforesaid requirement is satisfied that the concentrate provided for the balancing chamber stroke therefore also actually moves into the balancing chamber half to be filled with fresh dialysis solution.

This object is achieved by a dialysis machine having the features described herein.

Provision is accordingly made that the filling volume of a balancing chamber corresponds to or exceeds the sum of the volume of the mixing chamber and the inner volume of the dialysate line that extends from the mixing chamber to the balancing chamber. If the line from the mixing chamber to the balancing chamber is one or more tubes, it applies:

$$V(\text{MixC})+\text{Inner volume of the tube or tubes}<=V(BC)$$

where V(MixC) is the volume of the mixing chamber, i.e. the volume of the first subsection of the air separator and V(BC) is the filling volume of a balancing chamber of the balancing system.

For the case that V(BC) is larger than said sum, further water can be conveyed from the recirculation circuit or from the second subsection of the air separator into the balancing chamber half or into the balancing chamber.

It can in any case be ensured in accordance with the invention that the mixing ratio is correct.

The clocking of the balancing system and of the concentrate pumps preferably takes place such that the latter are activated when the balancing system, i.e. the balancing chamber, is just connecting the empty balancing chamber half to be supplied with fresh dialysate, i.e. at the beginning of a balancing chamber cycle. Reference is made to the above statements on the operation of the balancing chamber with respect to the term "empty". All the concentrate that is introduced or injected into the first subsection is directly "entrained" into the balancing chamber half; the transfer thus preferably takes place simultaneously.

One or more pumps, in particular membrane pumps, reciprocating pumps, etc. are preferably provided for conveying concentrate from the concentration source or sources into the mixing chamber.

The air separator preferably has a second subsection that can be a component of the recirculation circuit or of the water inlet system, with a line leading off from this second subsection to remove air from the air separator.

The second subsection is preferably located above the first subsection in the operating position of the air separator so that air that is located in the first subsection moves through a separation element that separates the first subsection from the second subsection into the second subsection and can be conducted away from there through said line. The separation element can here satisfy the function that the supplied concentrates remain at least very largely in the first subsection.

As can be seen from FIG. 4 that can partly or completely show an embodiment of the present invention, this line can open into the container 20 from which the recirculation circuit is fed with liquid, in particular with RO water (RO=reverse osmosis).

The present invention furthermore relates to an air separator for use in a dialysis machine, for example in a dialysis machine in accordance with one of the claims 1 to 3, wherein the air separator has a first subsection that serves as a mixing chamber, wherein the air separator has connectors via which the first subsection is connectable to at least one concentrate line and via at least one dialysate line to a balancing system of the dialysis machine and has a second subsection that has at least one connector by means of which the second subsection s connectable to a water inflow of the dialysis machine, wherein an at least partly conical separation disk is located between the subsections whose conical section extends into the first subsection. The air separator can also have one or more connectors by means of which the second subsection is connectable or connected to the water inlet system, preferably to a recirculation circuit, in particular a water recirculation circuit of the dialysis machine. The air separator can have a degassing drainage line by means of which air separated in the air separator can be discharged.

The term "separation disk" is generally to be understood as a "separation element" in any desired form and is not restricted to a disk shape, although it is not precluded that the separation disk is regionally designed in disk shape.

The separation disk is therefore designed such that the conical region projects into the mixing chamber, i.e. into the first region of the air separator. A tapering structure, i.e. a structure reducing in size in the cross-sectional area starting from a bottom area, is to be understood under the term "conical region" in the framework of the invention, said structure not necessarily having to be designed as conical, although this is a preferred embodiment of the invention. A pyramid-shaped region or a truncated cone or a truncated pyramid are also "conical regions" in the sense of the invention, for example.

The walls of the conical region can be planar or straight or curved.

The mixing chamber preferably has one, two or more connectors or supply lines for the concentrate. The conical region is preferably arranged such that its tip is directed in the direction of the connectors.

Air can rise at the obliquely extending walls of the conical region and can e.g. be conducted to channels or openings that are located in the separation disk. They are preferably arranged in a flat, flange-like region of the separation disk that extends around the conical region. The air in this manner moves into the second subsection of the air separator and can be separated therefrom via a line or a valve, etc. In a flat, i.e. non-conical structure, there is the risk that the air accumulates underneath the separation disk. This could be resolved upon provision of a plurality of bores in the separation disk, which would, however, entail the disadvantage that an undesirably large amount of concentrate would move from the first subsection into the second subsection of the air separator.

It is conceivable that the through opening or through openings are flowed over due to the forced convection during the recirculation phase. Air that may be located in the mixing region of the chamber is sucked through the opening (s) from the mixing chamber by Venturi effect. The opening (s) in the separation disk preferably face in the direction of the circulation in the upper region of the mixing chamber, i.e. the openings are disposed obliquely in the separation disk.

The oblique feed-through of the opening(s) in the separation disk results in the mixing phase, i.e. in the phase in which the concentrates are injected, in a circulation in the region in the mixing region of the chamber that covers the total lower volume of the mixing chamber and provides an almost complete flushing of the mixing chamber in the mixing phase.

The openings, i.e. the through bores, are preferably evenly distributed in the separation disk over its circular radius (e.g. three openings at an interval of 120°). This arrangement likewise provides a complete flushing of the total lower volume of the mixing chamber or of the total mixing chamber, with air that is located directly below the separation disk being drained off through the one or more openings in the recirculation phase.

The first subsection is preferably below the second subsection with respect to the standing arrangement or to the operating arrangement of the air separator, which brings along the advantage that the air to be removed flows independently from the first subsection into the second subsection.

To enable the passage of air from the first subsection into the second subsection and conversely the inflow of liquid or water, preferably RO water, from the second subsection into the first subsection, one or more through openings can be located in the separation disk through which air moves for the purpose of the air separation from the first subsection into the second subsection and/or through which water moves for the purpose of the preparation of the dialysis solution from the second subsection into the first subsection.

As stated above, it is preferred for the separation disk to have a conical section and a flange-like or disk-shaped section extending around it, with the one or more through openings being arranged in the flange-like or disk-shaped section.

To achieve a best possible mixing or swirling in the mixing chamber, provision can be made that the connector of the first subsection for the supply of the concentrate is not aligned with the connector of the first subsection for removing the dialysate, but is arranged laterally offset therefrom. Provision can be made for the same reason that the connector of the first subsection for the supply of the concentrate is not aligned with the cone tip, but is arranged offset therefrom. In this case, the concentrate does not impact the cone tip, but a region laterally offset therefrom.

It is generally of advantage that the connectors are arranged such that a circulating liquid flow arises in the first subsection.

The connector or connectors through which the concentrate or concentrates can be introduced into the mixing chamber can project into the mixing chamber 110. Its or their outlet height or outlet heights can preferably be arranged above an outlet opening of the primary air separator 50 to the line with a vertical arrangement. The risk that air possibly conveyed via the concentrate line can move into the balancing chamber via the line 58, for example with an empty container, can thereby be reduced or eliminated since the air would be supplied above the outlet 58.

The one or more through bores can extend perpendicular to, sloped to, or twisted with respect to the standing arrangement of the air separator, or be constructed as such. It is conceivable that the liquid entering from the second subsection enters into the mixing chamber with a spin so that mixing is as good as possible.

It is furthermore advantageous for the air separation if there is a spacing between the tip of the conical section of the separation disk and the bottom of the first subsection into which the conical section projects.

The air separator preferably has an integrated construction in that it is composed of at least two housing parts and in that a sealed seat is provided in the region of the connecting point of the two housing parts in which the separation disk is located. An air separator is thereby created with minimal space requirements. In addition, a clearly defined and stable position of the separation disk and thus also a defined volume of the mixing chamber is achieved and the air separation properties are only subject to slight fluctuations.

The present invention further relates to a dialysis machine in particular a dialysis machine as described herein, comprising a balancing system that has at least one balancing chamber for a volumetrically exact supply and removal of dialysis solution to and from a dialyzer fluidically connected to the balancing system in operation; a water inlet system connected to the balancing system for the supply of fresh dialysis liquid, with the water inlet system having an apparatus for degassing water that is connected to an air separator of the dialysis machine, with a first subsection of the air separator serving as a mixing chamber and being connectable to at least one concentrate source via at least one concentrate line and being in fluid communication with the balancing system via at least one dialysate line 58, wherein the air separator is configured as further described herein.

The invention further relates to a method of preparing a dialysate using a dialysis machine as described herein, wherein, on the filling of the balancing chamber, a volume of dialysate is supplied from the mixing chamber of the air separator that corresponds to or exceeds the sum of the volume of the mixing chamber of the air separator and the inner volume of the dialysate line extending from the mixing chamber to the balancing chamber. As stated above, it is thus achieved that the total volume provided for a balancing chamber stroke, i.e. for a complete filling of a balancing chamber, is also actually conducted to the balancing chamber to be filled and the mixing ratio of the components between one another is correct.

The invention furthermore relates to a method of preparing a dialysis solution using a dialysis machine as described herein, wherein some of the concentrate located in the mixing chamber of the air separator (50) is supplied to the water inlet system such as to its recirculation circuit—where present. This can be achieved, for example, by the spacing of the separation disk from the introduction point of the concentrate or concentrates into the mixing chamber, by the size and/or number of the openings in the separation disk that connect the two subsections of the air separator to one another, by the shape of the conical region, e.g. by the gradient of the walls of the conical region, by the water flow through the water inlet system or through the recirculation circuit, by the concentration injection speed, by the speed with which the dialysis solution is removed, etc. The advantage of the inflow of concentrate into the water inlet system or into the recirculation circuit comprises the service life of the components located in the water inlet system or in the recirculation circuit, in particular the degassing pump, and here in particular of its gear pump blades consisting of steel, being increased with respect to the operation in ultrapure RO water.

The entrance of concentrate into the water inlet system or into the recirculation circuit can take place to a degree such that the water located therein or the solution has a conductivity in the range from 0.15 to 0.2 μS.

The present invention further relates to a dialysis machine as described herein, wherein control means such as pumps, valves, etc. are provided that are configured to set the supply rate of fluid into the mixing chamber and the removal rate of fluid from the mixing chamber such that some of the liquid located in the mixing chamber is conduced to the water inlet system. A "net excess" of liquid thus remains that moves through the separation disk or its openings into the water inlet system or into the recirculation circuit.

It is pointed out at this point that the terms "a" and "one" do not necessarily refer to exactly one of the elements, even though this represents a possible embodiment, but can also designate a plurality of elements. The use of the plural equally also includes the presence of the element in question in the singular and, conversely, the singular also includes a plurality of the elements in question.

BRIEF DESCRIPTION OF THE DRAWINGS

Further details and advantages of the invention will be explained in more detail with reference to an embodiment shown in the drawing.

There are shown.

DETAILED DESCRIPTION OF THE PREFERRED EMBODIMENTS

Figure 1:
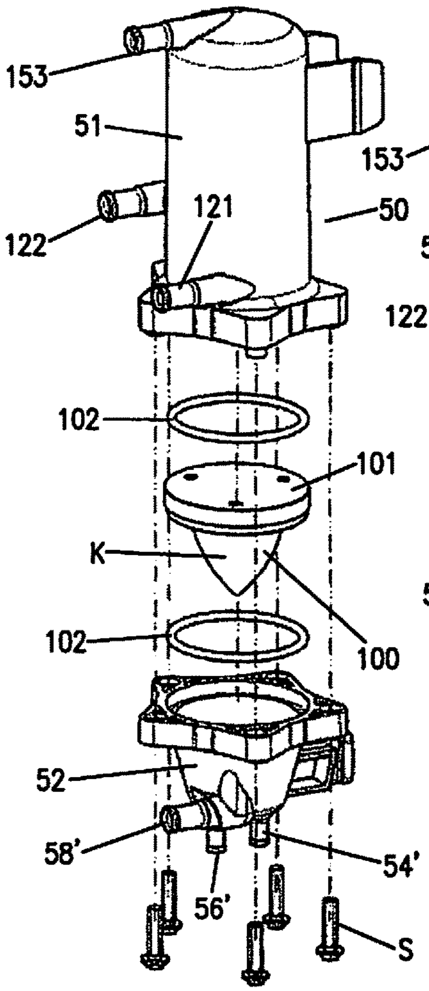
FIG. 1: an exploded representation of an air separator in accordance with the present invention.

FIG. 1 shows an embodiment of the air separator 50 as an exploded view.

It is pointed out that the same elements or elements of the same function are provided with the same reference numerals in the Figures.

It comprises an upper housing part 51 and a lower housing part 52 connected thereto by a screw connection (cf. screws S in FIG. 1). Both housing parts 51, 52 each have a flange, with the flanges being screwed to one another. The separation disk 100 is located between the housing parts 51, 52.

The separation disk 100 has a planar upper side and a lower side from which a conical region K extends in downward direction. The separation disk 100 furthermore has a disk-shaped peripheral flange 101 that is received between peripheral seals 102 that are pressed onto the flange 101 at the top and at the bottom such as can in particular be seen from FIG. 2.

The first subsection 110, i.e. the mixing chamber, is located below the separation disk 100 and the second subsection 120 of the air separator 50 is located above the separation disk 100.

Figure 2:
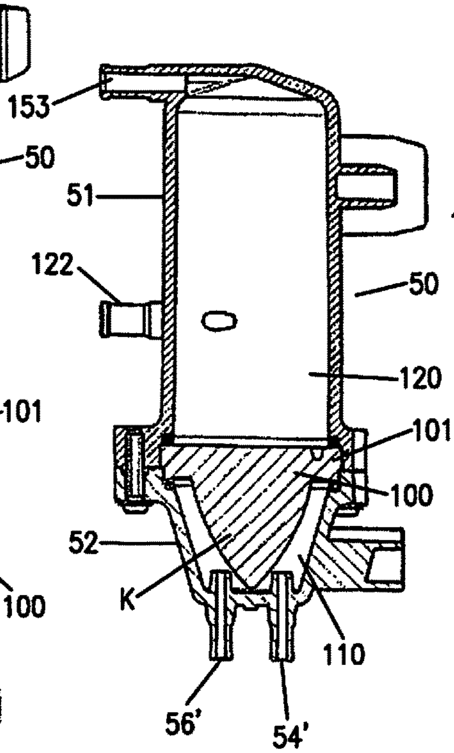
FIG. 2: a schematic sectional view through an air separator in accordance with the present invention.
Figure 3:
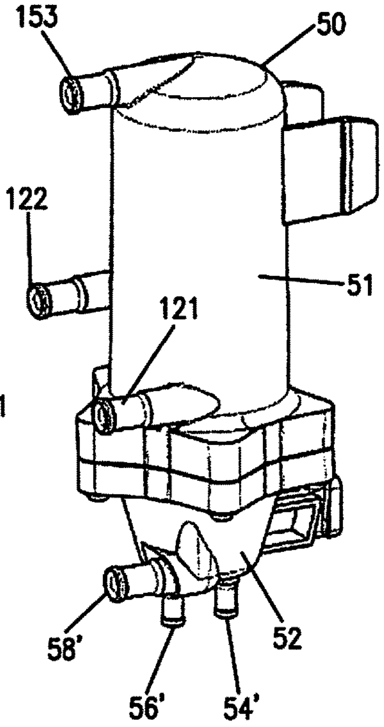
FIG. 3: a perspective view of the air separator in accordance with FIGS. 1 and 2.

As can be seen from FIGS. 1 and 2, the mixing chamber has two connectors 56' and 54' for the concentrate lines 56 and 54 (cf. FIG. 3). The two connectors extend perpendicularly in an upward direction and are offset from the tip of the conical region K. This offset and the conical structure facilitate the air separation from the mixing chamber. The air moves upwardly along the wall of the conical structure and moves through openings in the region 101 into the second subsection 120.

The connector 58' to which the dialysate line 58 extending to the balancing system B is connected extends perpendicular thereto.

The connector or connectors 56', 54' via which the concentrate or concentrates can be introduced into the mixing chamber 110 can project into the mixing chamber 110. The outlet height of the connector 56' and/or of the connector 54' can be arranged above an outlet opening 58' of the primary air separator 50 to the dialysate line 58 with a vertical arrangement. The risk that air possibly conveyed through the concentrate line can enter the balancing chamber via the line 58, for example with an empty canister, can thereby be reduced or eliminated since the air would be supplied above the outlet 58'.

The second subsection 120 has an inflow connector 121 and an outflow connector 122, with the RO water entering into the second subsection 120 through the inflow connector 121 and exiting the second subsection 120 again after passing through the second subsection 120 through the outflow connector 122. The second subsection 120 thus represents a component of the recirculation circuit 10.

If RO water is required for filling the balancing chamber half, some of the RO water flows out of the region 120 into the mixing chamber 110.

An exhaust air connector 123 to which the line 52 is connected via which the air is led off is located in the topmost region of the second subsection 120.

Openings or apertures are located in the flange-like region 101 of the separation disk 100 which connect the two subsections 110, 120 to one another and through which air moves out of the mixing chamber 110 into the second subsection 120 and through which RO water moves from the second subsection 120 into the first subsection 110. It is mixed there with the concentrates, preferably with an acid concentrate and with a base concentrate, and is then conducted into a balancing chamber half of the balancing system B.

The balancing system B consists of two balancing chambers that are operated alternately to one another, with each of the balancing chambers consisting of two balancing chamber halves each that are separated from one another by a movable membrane so that on the filling of the one balancing chamber half, the emptying of the other balancing chamber half takes place, such as is known from the prior art.

To ensure that the total concentrate introduced by the membrane pumps 54, 56 into the mixing chamber 110 is introduced for the respective balancing chamber cycle, a liquid volume is transferred into the balancing chamber on each balancing chamber stroke that is greater than or equal to the sum of the volume of the mixing chamber 110 and the volume of the line 58 that extends from the mixing chamber 110 to the balancing chamber to be filled.

Figure 4:
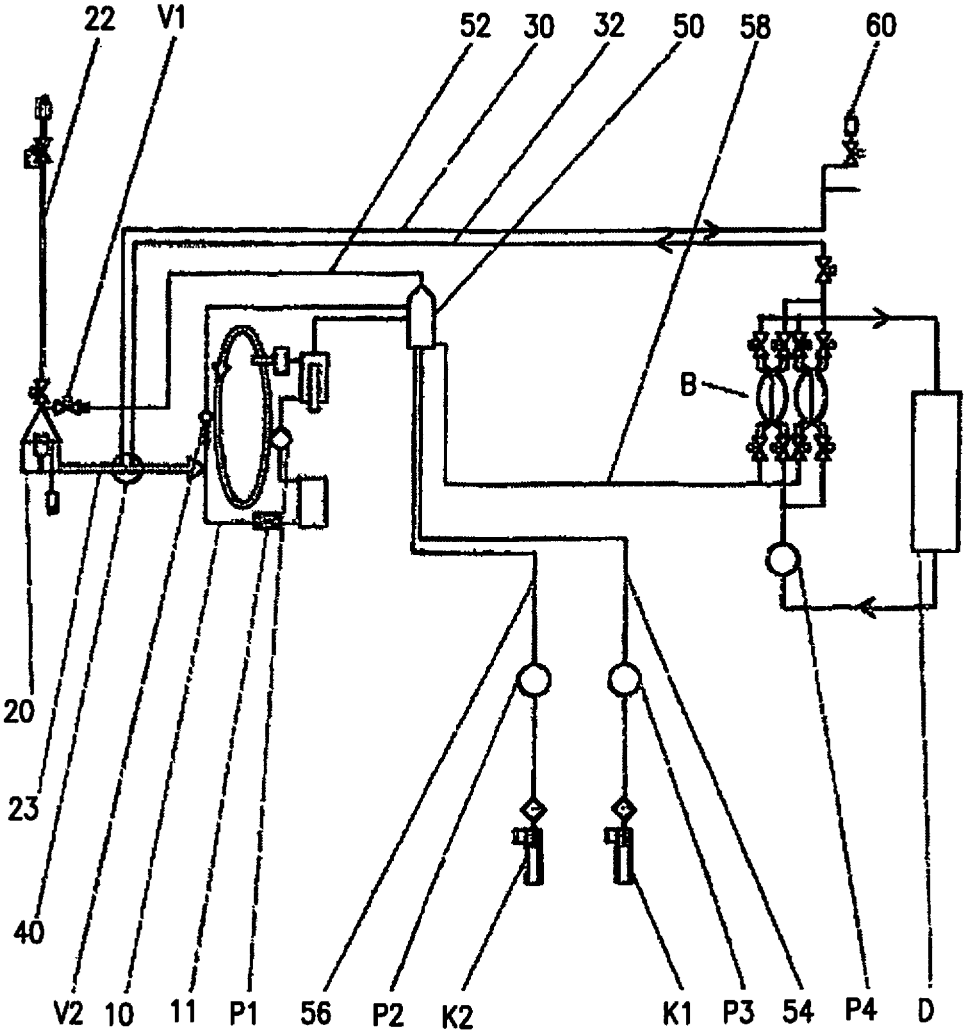
FIG. 4: a schematic view of a hydraulic system of a dialysis machine.

A combining of water, the acid concentrate, and the base concentrate in the mixing chamber or then downstream in the balancing chamber can, as shown, for example, in FIG. 4, be implemented by means of two concentrate pumps P2, P3 for supplying the acid concentrate and the base concentrate.

Alternatively to this, the acid concentrate and the base concentrate can be supplied to the balancing system B sequentially, i.e. after one another. It is thereby possible to save a concentrate pump. This approach is generally known from WO2018036859. This approach of a sequential metering is in this respect not restricted to a special hydraulic system or to a special mixing chamber, in particular not to the embodiments shown in FIGS. 1 to 4, but can rather also be used while utilizing other hydraulic systems and mixing chambers.

Figure 5:
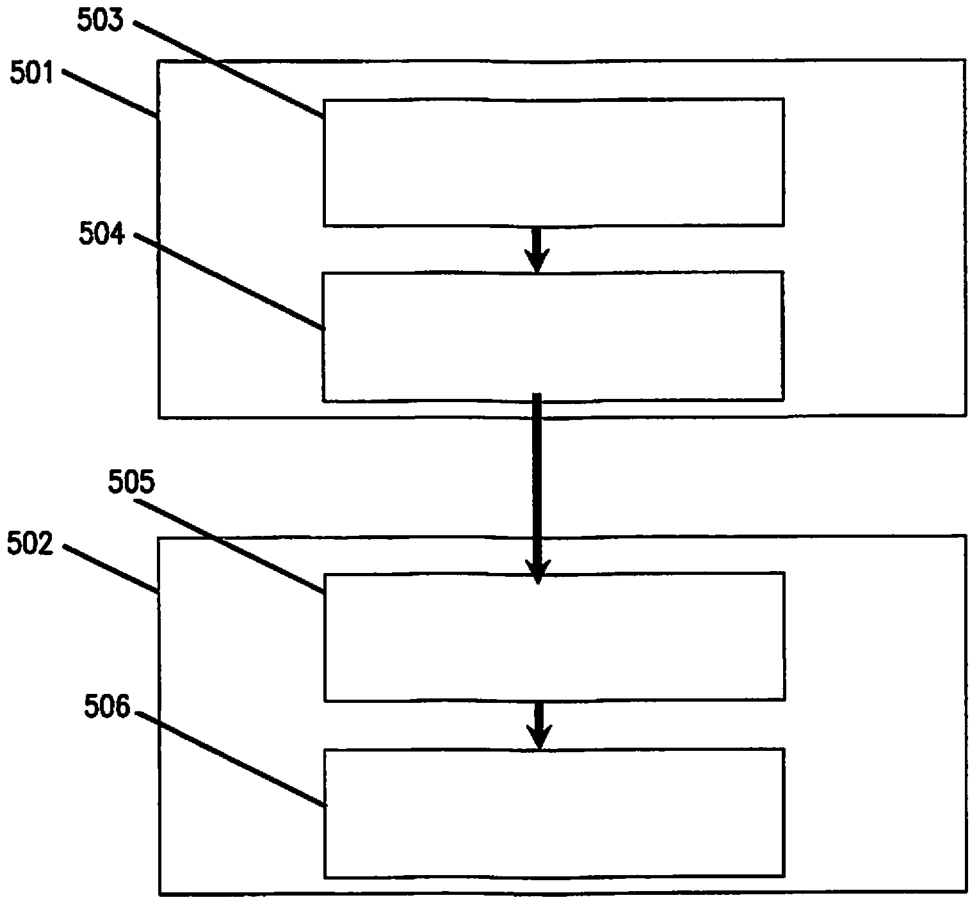
FIG. 5: a flowchart for a method of manufacturing a dialyzate from concentrates.

It has been recognized in a further development of the sequential metering that the following metering procedure results in a reliably determined dialysate composition. Not all the components of acid concentrate, base concentrate, and water are already combined in the balancing chamber in this process, illustrated with reference to FIG. 5:

- Step 1, reference numeral 501 in FIG. 5: The first concentrate is introduced into the balancing chamber with water in a first step, is mixed, and is expelled from the balancing chamber;
- Step 2, reference numeral 502 in FIG. 5: The second concentrate is introduced into the balancing chamber with water, is mixed, and is expelled from the balancing chamber.

Both Step 1 and Step 2 can each be divided into two sequential steps. This sequence has the advantage that the lines flowed through by both the first concentrate and the second concentrate can be flushed by the water and that it can thus be achieved that the total supplied concentrate is transferred into the balancing chamber and there is not already a mixing between the first concentrate and the second concentrate in the supply line to the balancing chamber. The first concentrate can be an acid concentrate and the second concentrate can be a base concentrate or vice versa:

- Step 1a, reference numeral 503 in FIG. 5: Supply of the first concentrate
- Step 1b, reference numeral 504 in FIG. 5: Supply of the water
- Step 2a, reference numeral 505 in FIG. 5: Supply of the second concentrate
- Step 2b, reference numeral 506 in FIG. 5: Supply of the water In the sequential steps 1a, 1b, 2a, 2b, it is also always only one liquid that is conveyed so that the second concentrate pump can also be dispensed with and it is possible to manage with only one pump arranged in the main line with which all the components of first concentrate, second concentrate, and water can be supplied.

With such a sequential supply, the correct amounts of first concentrate and second concentrate and water have to be supplied so that the completed dialysate has the correct composition. It must be noted here that a balancing chamber has a predefined volume. If this correct composition for a balancing chamber volume, for example, corresponds to a volume A of the acid concentrate, a volume B of the base concentrate, and a volume P of the water (where A+B+P=Balancing chamber volume), the following amount can be supplied on a supply in accordance $P_{rest}$) with Steps 1 and 2: Step 1: (2A+ and Step 2: (2B+$P_{rest}$) or Step 1: (2B+$P_{rest}$) and Step 2: (2A+$P_{rest}$). $P_{rest}$ is here in each case the volume of water that is required to fill the balancing chamber completely. It is thereby achieved that the ratio of the components overall to one another corresponds to the complete dialysate solution, in the above example (2(A+B+P)). In other words—with the sequential supply in accordance with Steps 1 and 2, twice the amount of concentrate can be supplied both for the first concentrate and for the second concentrate that would be required to prepare a volume of a balancing chamber of complete dialysis solution.

A mixture of the liquids expelled from the balancing chamber to form a dialysate ready for use can be achieved in that a mixing chamber can be provided downstream. This mixing chamber can be a separate chamber only provided for this function. The mixing chamber can also be a filter. The filter can comprise a semipermeable membrane, for example in the form of one or more porous plates or fibers. The porous membrane divides a container into a first chamber into which the liquid can be supplied coming from the balancing chamber and into a second chamber from which the liquid can flow out after passing through the membrane. Since the membrane provides a flow resistance to the liquid, it is possible that the liquids sequentially supplied from the balancing chamber are at least partially mixed, preferably completely mixed, in the first chamber. As can be seen with reference to FIG. 4, a plurality of balancing chambers connected in parallel can also be used.

Figure 6:
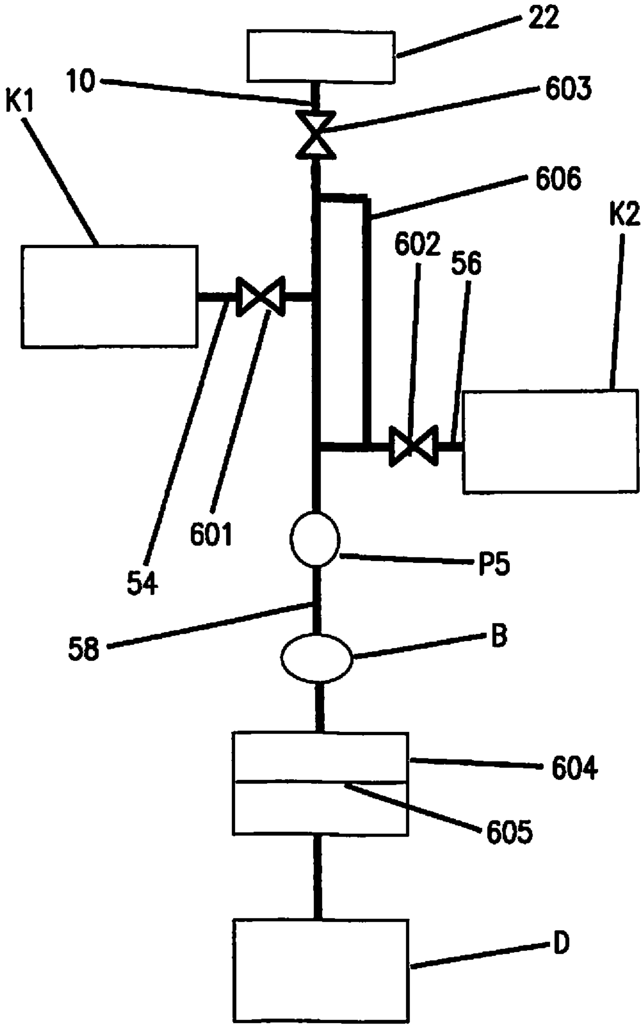
FIG. 6: a schematic view of an embodiment of a hydraulic system of a dialysis machine in accordance with the present invention.

An embodiment of a hydraulic system by which the serial supply of the concentrates and of the water can be implemented is illustrated in FIG. 6. Elements that functionally correspond to those of the hydraulic system shown in FIG. 4 are marked by the same reference numerals. The hydraulic system can be connected to a controller, for example in the form of a computer, that controls the carrying out of the above-described steps 1 and 2 or 1a, 1b, 2a, 2b by a corresponding control of the elements.

The hydraulic system has the water feed line 22, connectable to a water source, for example to an RO water supply, and the recirculation and degassing circuit 10, the balancing system B that comprises at least one balancing chamber, the first concentrate container K1 for the first concentrate, the second concentrate container K2 for the second concentrate, the first concentrate line 54 for the first concentrate, the second concentrate line 56 for the second concentrate, and the line 58 for supplying the liquids to the balancing chamber. It must be noted in this respect that the line 58 in accordance with this embodiment is not a dialysate line in a narrow sensor since due to the sequential supply of the liquids in this line, all three of them are not present at the same time. The hydraulic system is fluidically connected to the dialyzer D during the treatment.

The sequential supply in accordance with the above-described steps 1 and 2 can be carried out while using separate pumps for each liquid, for example in the hydraulic system of FIG. 4 the water by means of the pump P1 and the concentrates by means of the pumps P2 and P3. As stated above, the sequential supply permits the saving of pumps. As illustrated in FIG. 6, a pump P5 can be provided. The pump P5 can be arranged at the line 58.

Valves 601, 602, 603 are arranged at the first concentrate line 54, at the second concentrate line 56, and at the water feed line 10. These valves can be controlled by the control so that the liquids are supplied sequentially. The valve 601 can be open and the valves 602 and 603 can be closed, for example, in Step 1a. The first concentrate is supplied into the line 58 on pumping by pump P5. The valve 601 is closed and the valve 603 is open in Step 1b. The valve 602 remains closed. On pumping by pump P5, water is supplied into the line 58 and the first concentrate and water are supplied to the balancing chamber B. Since only water is supplied in Step 1b, the first concentrate is completely removed from the line system 58 and only water is present in the line section 58. The valve 603 is closed and the valve 602 is open in Step 2a. The valve 601 remains closed. The second concentrate is supplied into the line 58 on pumping by pump P5. The mixture of water and first concentrate is subsequently pumped from the balancing chamber B in the direction of the dialyzer. The valve 602 is closed and the valve 603 is open in Step 2b. The valve 601 remains closed. On pumping by pump P5, water is supplied into the line 58 and the second concentrate and water are supplied to the balancing chamber B. The mixture of water and second concentrate is subsequently pumped from the balancing chamber B in the direction of the dialyzer. Since only water is supplied in Step 2b, the first concentrate is completely removed from the line system 58 and only water is present in the line section 58.

The hydraulic system can, as described above, have a mixing chamber downstream of the balancing chamber. This mixing chamber can be a filter 604 having a semipermeable membrane 605 that divides the filter into two chambers. The completed dialysate, in particular the mixed dialysate, can be suppliable from the second chamber of the filter 604 to the dialyzer via a line.

A conductivity measuring device—not shown—can be arranged downstream of the mixing chamber. The correct composition can be monitorable by means of the conductivity measuring device in that, for example, the controller compares the measured conductivity with a desired value. Such a conductivity monitoring can be required to ensure that dialysate of the correct composition is always used in operation. To achieve this, the correct proportions of water, first concentrate, and second concentrate were previously always supplied to the balancing chamber. A simplification is achieved by the method described as new here and by the apparatus described as new here in that the path between the balancing chamber and the dialyzer is at least partially used, in particular the path between the balancing chamber and the conductivity sensor is at least partially used, to mix the first concentrate with the second concentrate.

In a further embodiment, likewise illustrated in FIG. 6, the hydraulic system can have a bypass line 606 for the water. This bypass line can be arranged such that water can be supplied from the water feed line 10 downstream of the valve 603 by which the water inflow can be controlled into the second concentrate line 56 downstream of the valve 602 by which the inflow of the second concentrate can be controlled. In this embodiment, the second concentrate line 65 opens downstream of the first concentrate line 54 into the line 58 that leads to the balancing chamber. In other words, the water feed line 10 has a branch to the bypass line 606 and the bypass line 606 has an inlet point in the second concentrate line 56.

With this arrangement, the water can also partially flush the connection region of the second concentrate line 56 into the balancing chamber feed line 58 free of the second concentrate with an open water valve 603 in Step 2b. It can thus be achieved that, in a subsequent Step 1a, the first concentrate that flows along the balancing chamber feed line 58 also does not come into contact with the second concentrate in the connection region of the second concentrate line 56. This can be necessary since the two concentrates can be concentrated acids and bases that can react with one another, for example, while forming a gas or while increasing the temperature.

The invention being thus described, it will be apparent that the same may be varied in many ways. Such variations are not to be regarded as a departure from the spirit and scope of the invention and all such modifications as would be recognized by one skilled in the art are intended to be included within the scope of the following claims.

The invention claimed is:

1. An air separator for use in a dialysis machine, the dialysis machine including a balancing system that has at least one balancing chamber for a volumetrically exact supply and removal of dialysis solution to and from a dialyzer fluidically connected to the balancing system in operation; a water inlet system connected to the balancing system for the supply of fresh dialysis liquid, with the water inlet system having an apparatus for degassing water that is connected to the air separator of the dialysis machine, with a first subsection of the air separator serving as a mixing chamber and being connectable to at least one concentrate source via at least one concentrate line and being in fluid communication with the balancing system via at least one dialysate line, the filling volume of a balancing chamber corresponds to or exceeds the sum of the volume of the mixing chamber and the inner volume of the dialysate line, the air separator comprising:

the first subsection that serves as the mixing chamber, connectors via which the first subsection is connectable to the at least one concentrate line and via the at least one dialysate line to the balancing system of the dialysis machine;

a second subsection that has an inflow region and a degassing drainage line; and an at least partly conical separation disk located between the first subsection and the second subsection, the at least partly conical separation disk comprising a conical section that extends into the first subsection, wherein one or more through bores are located in the at least partly conical separation disk through which air moves for air separation from the first subsection into the second subsection and/or through which water or a solution moves for preparation of the dialysis solution from the second subsection into the first subsection, and the one or more through bores extend or are designed obliquely with respect to a standing arrangement of the air separator.

2. The air separator in accordance with claim 1, wherein the first subsection is below the second subsection with respect to the standing arrangement of the air separator, with the degassing drainage line being arranged above the at least partly conical separation disk in the standing arrangement that corresponds to an operating state.

3. The air separator in accordance with claim 1, wherein the at least partly conical separation disk has the conical section and a flange-like section extending around it; and the one or more through bores are arranged in the flange-like section.

4. The air separator in accordance with claim 1, wherein the connector of the first subsection for the supply of the concentrate is not aligned with the connector of the first subsection for removing the dialysate, but is arranged offset therefrom; and/or the connector of the first subsection for the supply of the concentrate is not aligned with the cone tip, but is rather arranged offset therefrom.

5. The air separator in accordance with claim 4, wherein the connectors are arranged such that a circulating liquid flow arises in the first subsection.

6. The air separator in accordance with claim 1, wherein the one or more through bores extend obliquely such that a circulation flow in the mixing chamber is only or also formed by the liquid that enters into the mixing chamber through the one or more through bores.

7. The air separator in accordance with claim 1, wherein the one or more through bores are a plurality of through bores arranged so as to be distributed in a peripheral direction of the at least partly conical separation disk.

8. The air separator in accordance with claim 1, wherein a spacing is created between the tip of the conical section of the at least partly conical separation disk and a bottom of the first subsection.

9. The air separator in accordance with claim 1, wherein the air separator is composed of at least two housing parts; and a sealed seat in which the at least partly conical separation disk is located is provided in a region of a connecting point of the at least two housing parts.

10. The air separator in accordance with claim 1, with the dialysis machine further comprising one or more pumps provided for conveying concentrate from the at least one concentrate source connected in operation into the mixing chamber.

11. The air separator in accordance with claim 1, further comprising a line for removing air from the air separator that leads from the second subsection.

12. The air separator in accordance with claim 10, wherein the one or more pumps are membrane pumps.

13. A dialysis machine comprising a balancing system that has at least one balancing chamber for a volumetrically exact supply and removal of dialysis solution to and from a dialyzer fluidically connected to the balancing system in operation; a water inlet system connected to the balancing system for the supply of fresh dialysis liquid, with the water inlet system having an apparatus for degassing water that is connected to an air separator of the dialysis machine, with a first subsection of the air separator serving as a mixing chamber and being connectable to at least one concentrate source via at least one concentrate line and being in fluid communication with the balancing system via at least one dialysate line, the air separator being configured in accordance with claim 1.

* * * * *